(12) United States Patent
Johannsen

(10) Patent No.: US 6,217,874 B1
(45) Date of Patent: Apr. 17, 2001

(54) FAT COMPOSITIONS AND THEIR USE IN COSMETIC AND PHARMACEUTICAL EMULSION PRODUCTS

(75) Inventor: Frank Johannsen, Viby (DK)

(73) Assignee: Aarhus Oliefabrik A/S, Aarhus (DK)

( * ) Notice: Subject to any disclaimer, the term of this patent is extended or adjusted under 35 U.S.C. 154(b) by 0 days.

(21) Appl. No.: 08/119,058

(22) PCT Filed: Mar. 13, 1992

(86) PCT No.: PCT/DK92/00080

§ 371 Date: Sep. 15, 1993

§ 102(e) Date: Sep. 15, 1993

(87) PCT Pub. No.: WO92/16184

PCT Pub. Date: Oct. 1, 1992

(30) Foreign Application Priority Data

Mar. 15, 1991 (DK) .................................................. 0467/91

(51) Int. Cl.[7] ............................ A61K 35/78; A61K 31/19
(52) U.S. Cl. ......................................... 424/195.1; 514/557
(58) Field of Search .......................... 424/195.1; 514/557

(56) References Cited

U.S. PATENT DOCUMENTS

| | | | |
|---|---|---|---|
| 3,934,003 | * | 1/1976 | Tuma et al. ............................ 424/59 |
| 3,996,355 | * | 12/1976 | Lin et al. ................................ 514/86 |
| 4,035,519 | * | 7/1977 | Abou-Guendia ..................... 426/653 |
| 4,292,088 | * | 9/1981 | Scheuffgen et al. ................. 106/258 |
| 4,610,868 | * | 9/1986 | Fountain et al. ....................... 424/1.1 |
| 4,690,822 | * | 9/1987 | Uemura et al. ....................... 424/455 |
| 4,976,984 | * | 12/1990 | Yasukawa et al. ................... 426/602 |

FOREIGN PATENT DOCUMENTS

0191217 * 8/1986 (EP) .
0402090 * 12/1990 (EP) .

OTHER PUBLICATIONS

Grant & Hack's Chemical Dictionary (1987) pp. 230 & 407.*
Dialog Information Service, File 351, WPIL, Dial. acce. No. 007125526, WPIL acce. No. 87–125523/18.*
Dialog Information Service, File 351, Dial. acce. No. 007709852, WPIL acce. No. 88–343784/48.*

* cited by examiner

Primary Examiner—Howard C. Lee
(74) Attorney, Agent, or Firm—Michael L. Dunn

(57) ABSTRACT

A fat composition for cosmetic or pharmaceutical emulsion products, substantially consisting of a mixture of mono-, di- and triglycerides, wherein more than 90 weight % of the fatty acid residues incorporated in the glycerides contain 16–22 carbon atoms, produced from vegetable fats. The fat composition consists of a glyceride system A which is a mixture of mono-, di- and triglycerides having the composition 10–50 weight % of monoglyceride, 25–55 weight % of diglyceride and more than 10 weight % of triglyceride and having a hydroxyl number of 90–190 and an iodine number of 40–90, produced from unhardened or hardened vegetable fats or fractions thereof, preferably admixed with up to the same weight amount of a glyceride system B which is a mixture of mono-, di- and triglycerides having the composition 5–20 weight % of monoglyceride, 40–60 weight % of diglyceride and 20–50 weight % of triglyceride and having a hydroxyl number of 50–190 and an iodine number below 30, produced from hardened vegetable oils or fractions thereof. Hereby it is achieved that the fat composition serves both as an emollient, a stabilizer consistency imparting agent and coemulsifier in the emulsion product and that the consistency of the emulsion can be adjusted by varying the mixture proportion between the two glyceride systems in the fat composition.

13 Claims, No Drawings

FAT COMPOSITIONS AND THEIR USE IN COSMETIC AND PHARMACEUTICAL EMULSION PRODUCTS

The invention concerns a fat composition consisting of vegetable glycerides for use in cosmetic and pharmaceutical emulsion products as emollient, stabilizer, consistency imparting agent as well as coemulsifier. Such fat compositions represent alternatives in terms of applicability to fatty alcohols which have been found in certain cases'to cause skin trouble in the form of irritation and allergy (see references), and the fat compositions simultaneously serve as full or partial substitutions for traditional emollients.

In principle, cosmetic and pharmaceutical emulsion products consist of three components: a lipoid phase, a water phase and an emulsifier system. The lipoid phase contains primary emollients, e.g. triglycerides, alkanes (paraffin oils), silicone compounds, fatty acid esters, etc. The emulsifier system consists of a primary emulsifier and frequently a secondary emulsifier as well as one or more stabilizers and consistency imparting agents. The last two, however, are often included under the lipoid phase. In addition to distilled or demineralized water, the water phase often also contains components having special properties, e.g. with a view to maintaing the moisture of the skin. However, in some cases such components may also be present in the lipoid phase. Finally, perfume and preservative are often added in addition to antioxidant and optionally dyes.

Until now it has been necessary to use one type of components as emollients, a second type as emulsifiers, a third type as coemulsifiers and a fourth type as stabilizers and consistency imparting agents. To obtain the desired consistency in the final emulsion product it is necessary to mix the individual ingredients in carefully adapted ratios. Some known ingredients, however, have given two or three of these effects at the same time. It is thus known that fatty alcohols, such as cetyl and stearyl alcohol, serve both as a stabilizer, consistency imparting agent and coemulsifier in cosmetic emulsions.

It is likewise known from the cosmetic industry and food industry that mono-/diglycerides, e.g. palmityl or stearyl partial glycerides are active as consistency imparting agents and—with a suitably high monoglyceride content—as coemulsifiers.

Furthermore, a lipoid base is known from the patent literature (JP 60001111), consisting of mono-/di-/triglyceride based on fatty acids having an odd number of carbon atoms in the chain, i.e. synthetic fatty acids. This base is mentioned in the patent as being effective in the treatment of skin injuries caused by frost, but effects like the above-mentioned ones are not mentioned.

Another patent (JP 54049336) concerns a cosmetic cream containing glycerol esters of lanolin fatty acids which are claimed to have an emulsifying effect. The cream is reported to bring about a wet and soft skin feel. Stabilizing and consistency imparting effects are not mentioned.

The Japanese patent application (laid open) JP 63-258402 A concerns a glyceride composition which is reported to be suitable for cosmetic and pharmaceutical use. The glycerides according to this document are unique in containing 2-ethylhexanoic acid esterified with glycerol, and it thus does not involve vegetable glycerides, but synthetic glycerides containing a branched fatty acid residue. The advantages in use are reported to include extensibility and feel, while stabilizing and consistency imparting properties are not mentioned.

The object of the invention is to combine, in one and the same dermatologically safe, vegetable-based fatty base product, properties causing the product to serve both as an emollient, a stabilizer, consistency imparting agent and coemulsifier in cosmetic and pharmaceutical emulsion products, primarily for skin care.

This is achieved with the fat composition of the invention, which substantially consists of a mixture of mono-, di- and triglycerides, where more than 90 weight % of the fatty acid residues incorporated in the glycerides contain 16–22 carbon atoms, produced from vegetable fats, and which is characterized by consisting of a glyceride system A which is a mixture of mono-, di- and triglycerides having the composition 10–50 weight % of monoglyceride, 25–55 weight % of diglyceride and more than 10 weight % of triglyceride and having a hydroxyl number of 90–190 and an iodine number of 40–90, produced from unhardened or hardened vegetable fats of fractions thereof, preferably admixed with up to the same weight amount of a glyceride system B, which is a mixture of mono-, di- and triglycerides having the composition 5–20 weight % of monoglyceride, 40–60 weight % of diglyceride and 20–50 weight % of triglyceride and having a hydroxyl number of 50–190 and an iodine number below 30, produced from hardened vegetable oils or fractions thereof.

The fat compositions of the invention are preferably produced by mixing the glyceride systems A and B, characterized by following data:

|  | A | B |
| --- | --- | --- |
| Iodine number | 40–90 | 0–30 |
| Hydroxyl number | 90–190 | 50–190 |
| Glyceride composition, weight % |  |  |
| Mono | 10–50 | 5–20 |
| Di | 25–55 | 40–60 |
| Tri | >10 | 20–50 |

With these glyceride systems it is possible to control the consistency in an emulsion in a simple manner, the consistency being greatly determined by the mutual mixture proportion of the glyceride systems. To provide the emulsions, such as e.g. lotions 80–100 weight % of A and 0–20 weight t of B are advantageously used, with 85–95 weight % of A and 5–15% of B being preferred, and correspondingly 50–85 weight % of A and 15–50 weight % of B are advantageously used to provide thick emulsions, such as e.g. creams, the composition 55–70 weight % of A and 30–45 weight % of B being preferred. For use in emulsion products of intermediate consistency, e.g. soft creams, the fat composition preferably consists of a mixture 60–90 weight % of glyceride system A with 10–40 weight % of glyceride system B. the composition 70–85 weight % of A and 15–30 weight % of B being preferred.

The two glyceride systems can be produced according to the invention in the following manner:

Glyceride system A

This glyceride system is a mixture of mono-, di- and triglycerides produced from hardened and/or unhardened vegetable oils and fats or fractions thereof.

Conversion of the oils and fats to mono-, di- and triglycerides can take place by glycerolyzing them in a known manner in an apparatus adapted for the purpose at 150–300° C., preferably 200–270° C. with efficient stirring with 1–50 weight %, preferably 5–20 weight % of glycerol. The catalyst is a base, such as e.g. NaOH, KOH, Ca(OH)$_2$, CaO, Ca(AC)$_2$ or alkali metal salts of lower alcohols. Also soap may be used. The catalyst is used in an amount of up to 1 weight % of the fat amount. The glycerolysis is effected at a normal pressure in an inactive atmosphere. After the reaction has proceeded for 1–4 hours under the mentioned conditions to provide equilibrium, the reaction is stopped by cooling and neutralization of the catalyst with an equivalent amount of acid. Possible glycerol phase as well as neutralized catalyst are separated/filtered, and the fat phase is deodorized.

The raw materials for the fatty base are vegetable fats and oils whose fatty acid residues, as regards more than 90 weight % of them, contain 16–22 carbon atoms.

Particularly, suitable fats and oils are soybean oil, rapeseed oil, peanut oil, sunflower oil, cottonseed oil, and palm oil but also other may be used, such as fats or fractions thereof from fruits of the family Palmae and/or from seeds of one or more of the genera Garcinia, Pentadesma, Glycine, Carthamus, Olea, Brassica, Helianthus, Zea, Gossypium, Oryza, Shorea, Butyrospermum, Sesamum, Passiflora, Camelina, Limnanthes, Prunus, Triticum, Vitis, Arachis, Corylus, Persea, Madhuca, Juglans, Moringa, Macadamia, Papaver, Carica, Adenanthera, Trhevetia, Trigonella, Guisotia, Pinus, Hevea, Ricinodendron, Jatropha, and Tamarindus.

Oils and fats having natural iodine number between 40 and 90 can be used, but it is expedient to use oils/fats hardened in known manner to an iodine number between 40 and 90, it being expedient to harden selectively, i.e. in a manner such that di- and polyunsaturated fatty acids are converted to monounsaturated fatty acids to the greatest extent possible. This may be done in particular by using weakened nickel catalysts, e.g. by addition of small amounts of sulphur.

Particularly suitable fats for the fat composition are obtained by fractionating the hardened fats in a known manner, as described e.g. in the GB patent specification 1 219 245, but also other known fractionation methods may be used, e.g. dry fractionation or fractionation by means of detergents or by pressing the hardened fats to remove a fraction, which is liquid at the pressing temperature, from the solid part.

If the process described in the above-mentioned GB patent specification is used, 3 fractions having a low (LSF), intermediate (ISF) and high (HSF) melting point are obtained. According to the present invention, in particular LSF and HSF are used, and suitable mixtures contain 40–100 weight % of LSF and 0–60 weight % of HSF. Mixtures having 50–65 weight % of LSF and 35–50 weight % of HSF are particularly useful.

Commercially available palm oils and palm oleins lend themselves to being fractionated as described in the above-mentioned GB patent specification after hardening.

Glyceride system B

This glyceride system is a mixture of mono-, di- and triglycerides produced from the same oils/fats as are described under glyceride system A, but here hardened to an iodine number of 0–30. It should be mentioned that glyceride systems produced from commercially available high-melting fractions of palm oil (palm stearin) are suitable, and fractions having an iodine number below 3 can be used directly without hardening.

The glycerolysis is effected as described under glyceride system A, it being expedient to use 1–10 weight % of glycerol.

It applies to both glyceride systems A and B that the mixtures of mono-, di- and triglycerides can also be produced by esterifying fatty acid mixtures having the same composition as the fatty acid esters in the oils and fats described in a known manner with the calculated amount of glycerol.

The glycerolized product may be combined with up to 50 weight % of a non-glycerolized, possibly interesterified, hardened or unhardened, fractionated or non-fractionated fat originating from seeds and/or fruits of the family Palmae and/or at least one non-glycerolized, optionally interesterified, hardened, fractionated or non-fractionated fat originating from seeds of one or more of the genera Glycine Butyrospermum Sesamum, Passiflora, Camelina, Zea, Limnanthes, Oenothera, Borage, Prunus, Triticum, Vitis, Arachis, Corylus, Olea, Moringa, Carthamus, Juglans, Brassica, Cuphea, Macadamia, Aleurites, Allanblackia, Garcinia, Helianthus, Shorea, Madhuca, Oryza, Pentadesma, Papaver, Persea, Vaterica, Gossypium, Adenanthera, Thevetia, Carica, Trigonella, Guisotia, Pinus, Hevea, Ricinodendron, Jatropha, Tamarindus.

The fat composition of the invention should normally constitute 1–30 weight %, preferably 10–15 weight % of the emulsion product. It is unnecessary to incorporate other stabilizers and consistency imparting agents (e.g. partial glycerides), but such will normally not cause compatibility problems.

The fat composition of the invention may be emulsified together with a large number of known emulsifiers having HLB values of up to about 18, preferably between 8 and 17. Ethoxylated fatty alcohols and fatty acid esters, a large span in the EO chain distribution being acceptable, fatty acids as well as suitable combinations of these give good results when used in concentrations of 2–4 weight %.

Together with the fat composition of the invention the emulsion product may also contain liquid oils as an emollient, in particular vegetable triglycerides, but also derivatives thereof as well as paraffin oils, fatty acid esters, Guerbet alcohols, glycol ethers, etc. and combinations of these. Liquid oils or derivatives thereof may be incorporated in the emulsion product with up to about 30 weight %, preferably up to about 10 weight %.

The following examples illustrate various embodiments of the invention, but many other embodiments are possible.

| Examples Emulsion no. | | 160689-9 weight % | 210390-3 weight % | 140590-0 weight % |
|---|---|---|---|---|
| fatty base contents | A' | 10.0 | 10.0 | 6.0 |
| | B' | — | 2.0 | 6.0 |
| polyoxyethylene-10-hexadecanol | | 1.5 | 1.0 | — |
| polyoxyethylene-20-hexadecanoi | | 0.5 | — | — |
| polyoxyethylene-20-glycerylmonostearate | | — | 1.0 | — |
| polyoxyethylene-10-behenylether | | — | — | 3.8 |
| polyoxyethylene-40-hydrogenated castor oil | | — | 1.0 | — |
| paraffin oil | | — | — | 8.0 |
| sesame oil | | 7.0 | 6.0 | 6.0 |
| glycerol | | 3.0 | 3.0 | 3.0 |
| water, dem. | | 78.0 | 76.0 | 67.2 |
| Emulsion nature | | milk lotion/soft cream | | cream |
| Viscosity, mPa.s (Brookfield, spindle E, 6 rpm, 1 min) | | 7280 | 42200 | >100000 |

The glyceride systems A' and B', which are used in the above emulsions, have the following data:

|  | A' | B' |
|---|---|---|
| Monoglyceride, % | 44.5 | 6.6 |
| Diglyceride, % | 45.0 | 54.1 |
| Triglyceride, % | 10.5 | 39.3 |
| Iodine number (wijs) | 62.0 | 1.4 |
| Hydroxyl number | 163.0 | 67.0 |

The emulsions were produced by mixing glycerol and water with heating to about 78° C. The other ingredients were simultaneously heated separately with slow stirring (propeller stirrer) to about 73° C. (homogeneous fat phase). The water phase was gradually added to the fat phase with efficient stirring, it being carefully attempted to avoid entrapment of air in the emulsion. Subsequent emulsification (stirring) until the temperature had dropped to about 25° C. Homogenization not necessary. Drawing off.

After standing for 10–12 months at 20–30° C., these emulsions showed no sign of stability problems. In a trained panel consisting of 8 white women (24–47 years without skin diseases) the emulsions were evaluated and tested for the parameters A: gloss, B: structure, C: whiting tendency, D: ease of application, E: penetration ability and F: afterfeel. In each individual case 0.05 ml of test emulsion was applied to a 3×3 cm area of the upper side of the left hand and analogously a reference emulsion (see the following) on the upper side of the right hand. The parameters B, C and D were evaluated during the application. E was evaluated one minute and F 10 minutes after initial application. As a reference for the evaluation of the participants the following traditional composition based on fatty alcohol was used (produced analogously with the above-mentioned ones): Cetyl/stearyl alcohol 5.0 weight i, polyoxyethylene-10-hexadecanol 3.0 weight %, polyoxyethylene-25-hexadecanol 3.0 weight %, polyoxyethylene-40-hydrogenated castor oil 1.0 weight *, shea butter 4.0 weight %, isopropylmyristate 2.0 weight %, sesame oil 7.0 weight %, glycerol 3.0 weight %, water, dem. 72.0 weight: - soft cream, viscosity 29200 mPa.s.

The parameters were evaluated according to an integer scale from 1 to 9, where 1 was dull (A), heterogeneous (B), pronounced (C), difficult to distribute (D), poor—occlusive feel/felt like an extra layer on the skin (E) unpleasant—the skin felt greasy, sticky, rough, dry (F). 9 was bright (A), homogeneous (B), none (C), easy to distribute (D), good—the emulsion appeared to penetrate rapidly into the skin (E) pleasant—the skin felt elastic, smooth, soft but not greasy (F). The intermediate values represent relative graduations between these extremes.

Each individual was tested in a double blind test three times with each emulsion. The results appear from the following, the numbers representing simple averages (all test individuals) rounded off to an integer.

|  | 160689-9 | 210390-3 | 140590-0 | reference |
|---|---|---|---|---|
| A | 8 | 8 | 8 | 8 |
| B | 7 | 8 | 5 | 5 |
| C | 4 | 6 | 2 | 2 |
| D | 6 | 6 | 6 | 5 |
| E | 6 | 6 | 5 | 5 |
| F | 6 | 6 | 6 | 6 |

It will be seen that the emulsions based on the fat compositions of the invention were found to be equal to or better than the traditional fatty alcohol emulsion.

The irritation and allergy potential of the glyceride systems were tested on human skin in a test with 82 volunteers at Inveresk Research International Limited, Tranent EH 33 2NE, Scotland (IRI Project No. 580546). The employed method was in accordance with the one described by Shelanski and Shelanski (Shelanski, H.A. and Shelanski, M.V.: "A New Technique of Human Patch Tests", Proc. Sci. Section Toil. Group Assoc. 19, 1953)

The glyceride systems A' and B' were tested separately with para-tin oil and a cetyl/stearyl fatty alcohol, Hyfatol CS (cetyl/stearyl fatty alcohol min. 99% pure fatty alcohol a product of Aarus Oliefabrik A/S, Aarus, Denmark. The fatty alcohol composition is 0–3% $C_{14}$, 45–55% $C_{16}$, 45–55% $C_{18}$ and 0–3% $C_{20}$. The iodine number is max. 0.8.) as reference substances. The obtained irritation and allergy potential results are stated below.

| | Irritation potential | | | |
|---|---|---|---|---|
| | Total number of scores | | | |
| Test material | 0 | 1 | 1E | 2 |
| Glyceride system A' | 740 | 10 | 0 | 0 |
| Glyceride system B7' | 739 | 11 | 0 | 0 |
| Hyfatol CS | 735 | 13 | 0 | 2 |
| Paraffin oil | 744 | 6 | 0 | 0 |

Scores: 0 - no visible reaction
1 - mild erythematous reaction
1E - mild erythematous reaction with edema and/or papule
2 - moderate erythematous reaction

| | Allergy Potential | | | |
|---|---|---|---|---|
| | Total number of scores after | | | |
| | 48 hours | | 96 hours | |
| Test material | 0 | A | 0 | A |
| Glyceride system A' | 0 | 0 | 0 | 0 |
| Glyceride system B7' | 0 | 0 | 0 | 0 |
| Hyfatol CS | 1 | 1 | 1 | 1 |
| Paraffin oil | 0 | 1 | 0 | 0 |

O: applied to the arm used in the irritation study
A: applied to the other arm

It could be concluded that statistically the glyceride systems A' and B' are not more irritating than the reference substances and do not cause allergy. It is noted that the glyceride systems A' and B' had better total scores than the fatty alcohol.

References

M. Hannuksela; International Journal of Cosmetic Science, vol. 10, pp. 9–14, 1988.
W. G. van Ketel; Contact Dermatitis, vol. 11, pp. 125–6, 1984.

W. Keilig; Dermatosen, vol. 31, pp. 50–4, 1983.

A. Blondeel, J. Oleffe & G. Achten; Contact Dermatitis, vol. 4, pp. 270–6, 1978.

What is claimed is:

1. A fat composition consisting of from 100 to 50 parts by weight of a glyceride system A which is a mixture of mono-, di- and triglycerides having the composition 10–50 weight % of monoglyceride, 25–55 weight % of diglyceride and more than 10 weight % of triglyceride and having a hydroxyl number of 90–190 and an iodine number of 40–90, produced from unhardened or hardened vegetable fats or fractions thereof, and 0 to 50 parts by weight of a glyceride system B which is a mixture of mono-, di- and triglycerides having the composition 5–20 weight % of monoglyceride, 40–60 weight % of diglyceride and 20–50 weight % of triglyceride and having a hydroxyl number of 50–190 and an iodine number below 30, produced from hardened vegetable oils or fractions thereof.

2. A fat composition according to claim 1 consisting of a mixture of 50–85 weight % of glyceride system A with 15–50 weight % of glyceride system B.

3. A fat composition according to claim 1 consisting of a mixture of 80–100 weight % of glyceride system A with 0–20 weight % of glyceride system B.

4. A fat composition according to claim 1 consisting of a mixture of 60–90 weight % of glyceride system A with 10–40 weight % of glyceride system B.

5. The composition of claim 2 wherein the composition consists of 55–70 weight % of A and 30–45 weight % of B.

6. The composition of claim 3 wherein the composition consists of 85–95 weight % of A and 5–15 weight % of B.

7. The composition of claim 4 wherein the composition consists of 70–85 weight % of A and 1.5–30 weight % of B.

8. The fat composition of claim 1 wherein the glyceride systems A and B are produced from fats or fractions thereof selected from the group consisting of fats produced from fruits of the family Palmae and seeds of the genera Garcinia, Pentadesma, Glycine, Carthamus, Olea, Brassica, Helianthus, Zea, Gossypium, Oryza, Shorea, Butyrospermum, Sesamum, Passiflora, Camelina, Limnanthes, Prunus, Triticum, Vitis, Arachis, Corylus, Persea, Madhuca, Juglans, Moringa, Macadamia, Papaver, Carica, Adenanthera, Thevetia, Trigonella, Guisotia, Pinus, Hevea, Ricinodendron, Jatropha, and Tamarindus.

9. An emulsion product comprising an aqueous emulsion of a fat composition consisting of from 100 to 50 parts by weight of a glyceride system A which is a mixture of mono-, di- and triglycerides having the composition 10–50 weight % of monoglyceride, 25–55 weight % of diglyceride and more than 10 weight % of triglyceride and having a hydroxyl number of 90–190 and an iodine number of 40–90, produced from unhardened or hardened vegetable fats, or fractions thereof, and 0 to 50 parts by weight of a glyceride system B which is a mixture of mono-, di- and triglycerides having the composition 5–20 weight % of monoglyceride, 40–60 weight % of diglyceride and 20–50 weight % of triglyceride and having a hydroxyl number of 50–190 and an iodine number below 30, produced from hardened vegetable oils or fractions thereof.

10. The emulsion product of claim 9 wherein the fat composition consists of a mixture of 50–85 weight % of glyceride system A with 15–20 weight % of glyceride system B.

11. The emulsion product of claim 9 wherein the fat composition consists of a mixture of 80–100 weight % of glyceride system A with 0–20 weight percent: of glyceride system B.

12. The emulsion product of claim 9 wherein the fat composition consists of a mixture of 60–90 weight % of glyceride system A with 10–40 weight % of glyceride system B.

13. The emulsion product of claim 9 wherein the emulsion is an oil in water emulsion.

* * * * *

UNITED STATES PATENT AND TRADEMARK OFFICE
CERTIFICATE OF CORRECTION

PATENT NO. : 6,217,874 B1
DATED : April 17, 2001
INVENTOR(S) : Frank Johannsen

It is certified that error appears in the above-identified patent and that said Letters Patent is hereby corrected as shown below:

Claim 7,
Line 2, please change 1.5 to "15".

Claim 11,
Line 3, please delete the colon after "percent".

Signed and Sealed this

Thirteenth Day of November, 2001

Attest:

NICHOLAS P. GODICI
Attesting Officer
Acting Director of the United States Patent and Trademark Office